United States Patent [19]

Slaughterbeck

[11] Patent Number: 4,548,249

[45] Date of Patent: Oct. 22, 1985

[54] PROTECTIVE SLEEVE FOR SPHYGMOMANOMETER CUFF

[76] Inventor: Perry K. Slaughterbeck, Rte. 1, Box 259, Shelley, Id. 83274

[21] Appl. No.: 647,429

[22] Filed: Sep. 5, 1984

[51] Int. Cl.[4] .............................................. B65D 65/02
[52] U.S. Cl. .................................... 150/52 R; 150/53; 150/55; 128/686; 224/901
[58] Field of Search .................. 150/50, 52 R, 53, 55; 128/686, 724, 736; 224/222, 267, 901; 206/303, 305, 306, 363, 569, 570

[56] References Cited

U.S. PATENT DOCUMENTS

| 2,692,599 | 10/1954 | Creelman | 224/222 |
| 3,606,880 | 4/1969 | Ogle, Jr. | 128/680 |
| 3,757,772 | 9/1973 | Goldblat et al. | 128/686 |
| 3,810,466 | 5/1974 | Rogers | 150/53 |
| 4,108,310 | 8/1978 | Aldrige et al. | 206/305 |
| 4,197,944 | 4/1980 | Catlin | 128/736 |

Primary Examiner—Joseph Man-Fu Moy
Assistant Examiner—David Fidei
Attorney, Agent, or Firm—Harvey B. Jacobson

[57] ABSTRACT

An elongated flexible envelope having one open longitudinal margin is provided and is of a length and width to receive the flexible and inflatable strap-type body of a sphygmomanometer therein. One side of one end portion of the envelope includes first window defining structure and a first readily removable closure therefor, the other side of the other end of the envelope includes second window defining structure and a second readily removable closure therefor and the longitudinal margin of the envelope opposite the open longitudinal margin has an opening formed therein and an integral flexible tube portion has one end portion anchored to the envelope about the opening and a second end portion extending outwardly from the envelope. A sphygmomanometer strap-type body is receivable within the open longitudinal margin of the envelope with the attached bulb-type pump thereof and the associated valve equipped air line loosely receivable through the aforementioned opening and in the flexible tube portion. The window structures in the envelope are provided and openable in order that releasably engageable anchor structure carried by the opposite sides of the opposite ends of the inflatable, strap-type body of the sphygmomanometer may be releasably engaged with each other through the window structures after the latter are opened. In addition, the open longitudinal margin of the envelope includes structure whereby it may be removably closed.

10 Claims, 5 Drawing Figures

PROTECTIVE SLEEVE FOR SPHYGMOMANOMETER CUFF

BACKGROUND OF THE INVENTION

There are many clinics, hospitals and doctor's offices in which successive patients have their blood pressure taken. Conventional methods of blood pressure taking involve the utilization of sphygmomanometers which are encircled and anchored about a patient's limb and then inflated. This practice of blood pressure taking has been carried out for many years and is still the accepted method, other than more sophisticated methods which are available and used for constant blood pressure monitoring of critically ill patients.

When a patient enters a clinic, hospital or doctor's office for a specific complaint, the major concern of the attending doctor or nurse is the patient's stated complaint. However, such a person may have a communicable illness of which he or she is unaware and the usual practice of taking the blood pressure of substantially all patients can result in a communicable illness being inadvertently transmitted from one patient to another as a result of successive contact with such patients by a sphygmomanometer cuff.

Accordingly, a need exists for means by which the transfer of a communicable illness between patients upon which a sphygmomanometer cuff is successively placed may be eliminated, or at least substantially reduced.

To this end the instant invention has been developed and comprises an inexpensive disposal and flexible envelope into which a sphygmomanometer cuff, bulb-type pump and gauge may be inserted prior to the sphygmomanometer cuff being placed about the limb of a patient whose blood pressure is to be taken. The envelope includes one openable side through which the sphygomomanometer cuff may be inserted and removed and that openable side is provided with closure structure whereby it may be temporarily closed.

Examples of protective covers of various types for sphygmomanometer cuffs and other structures are disclosed in U.S. Pat. Nos. 2,758,593, 3,606,880, 3,757,772, 4,197,944 and 4,222,391.

BRIEF DESCRIPTION OF THE INVENTION

The protective cover of the instant invention is provided for use in conjunction with a sphygmomanometer cuff and is operable to substantially completely enclose the cuff and to prevent any possibility of direct contact contamination of the cuff by a patient around whose limb the cuff is secured. In this manner, the likelihood of the transmittal of a communicable illness from a first patient to a second patient upon whom the same sphygmomanometer cuff has been used is substantially eliminated.

The protective sleeve or cover is in the form of an elongated envelope open along one longitudinal marginal portion and into which a sphygmomanometer cuff may be readily placed. The open side of the envelope includes structure whereby it may be readily closed after a sphymanometer cuff has been received within the envelope and the longitudinal marginal portion of the envelope remote from the open side thereof includes an opening and a flexible tube member having one end secured to the envelope about the opening. In this manner, a bulb-type pump and associated valve and hose carried by a sphygmomanometer cuff received within the envelope can be loosely received through the opening in the side of the envelope remote from the open marginal portion of the cuff and further received in the aforementioned tube for actuation thereof through the tube from the exterior of the envelope.

The main object of this invention is to provide a protective sleeve for a sphygmomanometer cuff operable to substantially eliminate any possibility of transfer of a communicable illness, by contact, between patients upon whom the same sphygmomanometer cuff is successively used.

Another object of this invention is to provide a protective sleeve for a sphygmomanometer cuff which may be inexpensively produced and which may therefore be of the disposal.

Still another important object of this invention is to provide a protective sleeve or envelope for a sphygmomanometer cuff which is adapted for use in conjunction with sphygmomanometer cuffs of different manufacture.

A final object of this invention to be specifically enumerated herein is to provide a protective sleeve for a sphygmanometer cuff and which will conform to conventional forms of manufacture, be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

DETAILED DESCRIPTION OF THE INVENTION

Figure 1:
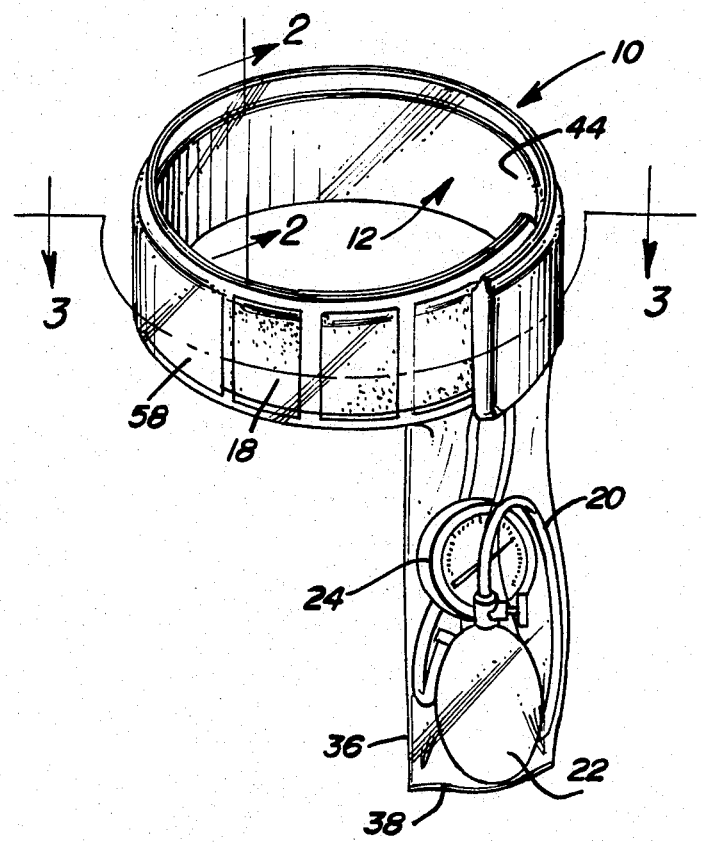
FIG. 1 is a perspective view of the protective sleeve with an associated sphygmomanometer cuff disposed therein.
Figure 2:
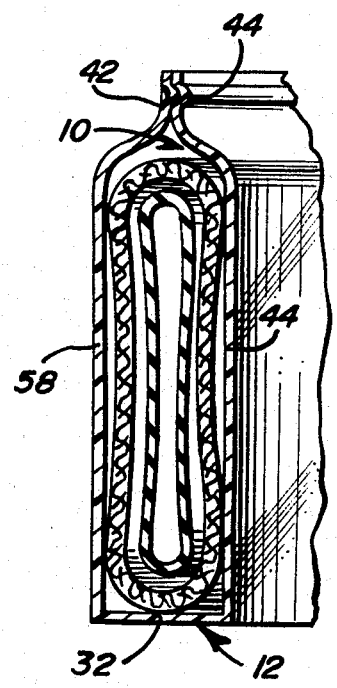
FIG. 2 is an enlarged vertical sectional view taken substantially upon the plane indicated by the section line 2—2 of FIG. 1.

Referring now more specifically to the drawings, the numeral 10 generally designates the protective sleeve of the instant invention having a typical sphygmomanometer referred to in generally by the reference numeral 12 enclosed therein.

Figure 3:
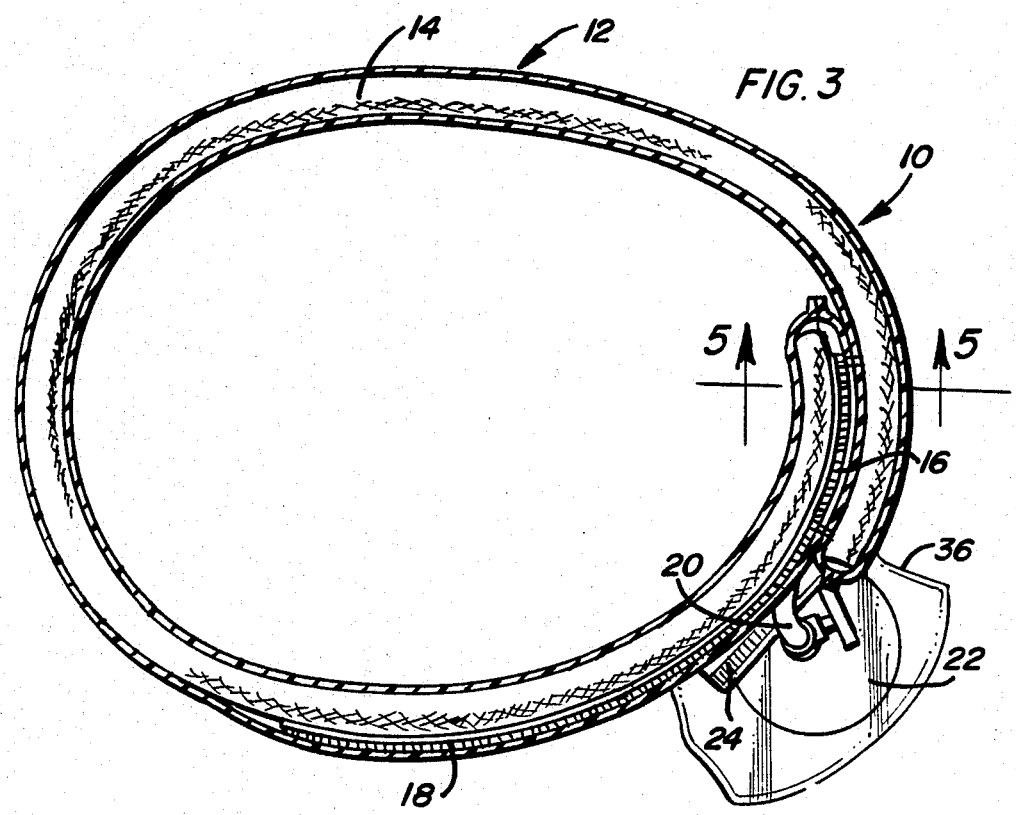
FIG. 3 is an enlarged horizontal sectional view taken substantially upon the plane indicated by the section line 3—3 of FIG. 1.

The typical sphygmomanometer 12 includes an elongated, flexible and inflatable strap-type body or cuff 14. One side of a first end of the body 14 has attaching means in the form of a Velcro patch 16 secured thereto and the other side of the opposite end of the body 16 includes second attaching means 18 in the form of a Velcro patch 18 mounted thereon. The Velcro patches 16 and 18 are releasably engageable with each other to retain the opposite ends of the body 14 in overlapped engagement with each other in the manner illustrated in FIG. 3 of the drawings. Of course, inasmuch as the Velcro patch 18 extends a considerable distance along the length of the body 14, the body 14 may be snugly secured about body limbs of different sizes.

The sphygmomanometer 12 further includes an inflation line or hose 20 having a valve equipped bulb-type pump 22 supported from one end and with the other end of the hose opening into the interior of the inflatable body 14. In addition, the sphygmomanometer 12 also includes a pressure gauge 24 communicated with the interior of the body 14 via a second flexible hose 26. Of course, different makes of sphygmomanometers utilize somewhat different pumps, valves and gauges and it is possible to operatively mount the gauge 24 on the hose 20 and thus do away with the hose 26.

Figure 4:
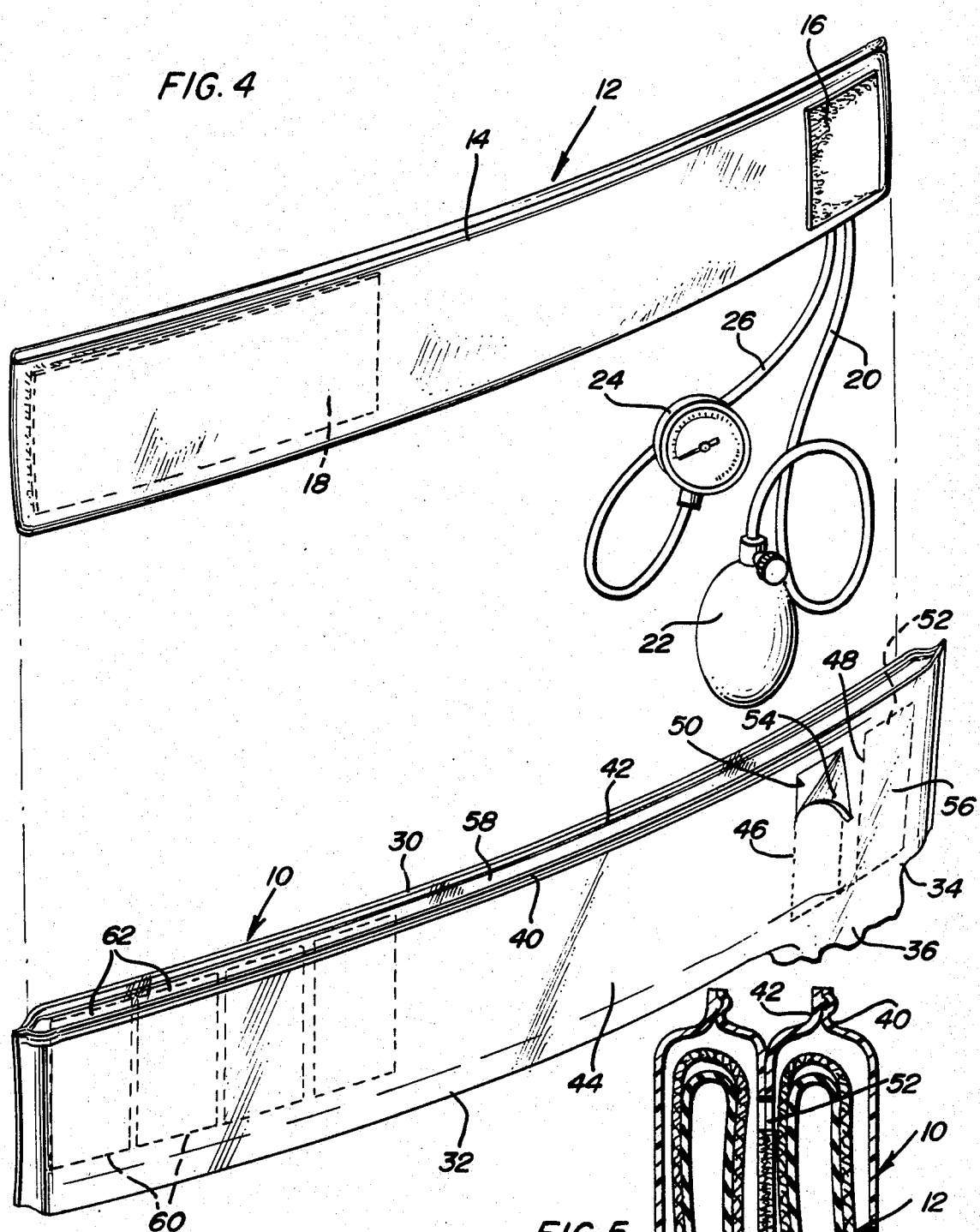
FIG. 4 is a fragmentary perspective view of the protective sleeve with an associated sphygmomanometer cuff is exploded position.
Figure 5:
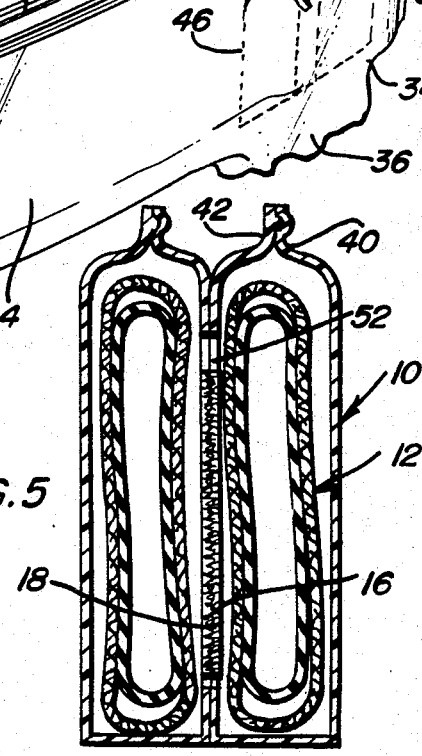
FIG. 5 is an enlarged vertical sectional view taken substantially upon the plane indicated by the sectional line 5—5 of FIG. 3.

The protective sleeve 10 comprises an elongated flexible envelope which is open along one longitudinal marginal portion 30 and in which the sphygmomanometer 12 is freely receivable in a manner which is believed to be obvious from FIG. 4 of the drawings. The envelope or sleeve 10 is closed along the longitudinal marginal portion 32 thereof opposite the marginal portion 30, but the marginal portion 32 includes an opening 34 formed therein. One end of a flexible tube 36 is secured to the longitudinal marginal portion 32 about the opening 34 and the end of the tube 36 remote from the opening 34 is closed as at 38, although the outer end of the tube 36 may remain open, if desired.

The open longitudinal marginal portion 30 of the envelope 10 is defined between a pair of corresponding marginal edge portions 40 and 42 of the envelope 10 and the marginal portions 40 and 42 include releasably engageable rib and channel portions which may be pressed together in the manner provided on "Zip-Loc" bags. In addition, marginal edge portions 40 and 42 may be provided with other conventional structures for releasably securing the marginal edge portions 40 and 42 together.

One end of a first side 44 of the envelope 10 is provided with a pair of rectangular weakened zones 46 and 48 defining window areas 50 and 52 which may be opened by removing those portions 54 and 56 of the first side 44 bounded by the zones 46 and 48. The patch 16, depending upon the make and model of the sphygmomanometer 12, will be registered with either one or both of the openings 50 and 52. In addition, the second side 58 of the envelope 10 remote from the first side 44 includes four similar rectangular weakened zones 60 from which portions 62 of the second side 58 may be removed in order to define similar window openings. The patch 18 is registered with all of the window openings which may be removed by the portions 62. Thus, the patches 16 and 18 may be exposed to the exterior of the envelope 10 in order that the patches 16 and 18 may be releasably engaged with each other in the manner illustrated in FIG. 3 of the drawings when the ends of the envelope 10 are disposed in overlapped engagement about a patient's limb.

The envelope 10 may be constructed of transparent material and the bulb-type pump 22 and associated valve may be actuated through the tube 36. Also, the gauge 24 may be visually read through the tube 36. If the end of the tube 36 remote from the envelope 10 is open, the bulb-type pump 22 and gauge 24 may project outwardly from the open end of the tube and thus be actuated and visually read, respectively, exteriorly of the tube 36.

When the envelope 10 is to be used, the longitudinal marginal portion is opened and the sphygmanometer 12 is placed within the envelope 10 with the pump 22 and gauge 24 received in the tube 36. Then, the desired portions 54 and 62 may be removed to expose the corresponding pads 16 and 18 and the sphygmomanometer 12, disposed within the envelope 10, may be placed about the limb of a patient after the marginal portion 30 has been closed. The blood pressure testing and reading operation may then be carried out without contact contamination of the sphygmomanometer by the limb of the patient about which the envelope is disposed and after the blood pressure testing operation is completed, the sphygmomanometer 12 and envelope 10 may be removed from about the patient's limb and the sphygmomanometer may be removed from the envelope 10 before disposal of the latter. Of course, the sphygmomanometer 12 is placed within a new envelope or sleeve 10 before its subsequent use on another patient.

It is also to be noted that means other than "Zip-Loc" marginal portions 40 and 42 may be used to removably close the envelope and that releasably engageable fastening means other than the "Velcro" patches 16 an 18 may be used to removably secure the cuff 14 about a body limb. Further, it is also to be noted that means other than the closure being on the opposite longitudinal margin from the flexible tube portion may be used to removably close the envelope. Finally, means other than rectangular weakened zones may be used to define window areas in the envelope.

The foregoing is considered as illustrative only of the pinciples of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A protective sleeve for a sphygmomanometer of the type including a flexible, elongated and inflatable strap-type body having inner and outer sides, coacting first and second fastener means on the inner and outer sides of first and second ends, respectively, of the body for adjustably overlappingly and removably securing the opposite ends of said body together to form a closed band of adjusted peripheral size and including a bulb-type air pump and fluid pressure release assembly communicated with the interior of said body by a flexible hose extending therebetween, said sleeve comprising an elongated flexible envelope having an open longitudinal margin and being of a length and width to receive said strap-type body therein, one side of one end portion of said envelope including first means defining a first window opening therein and a first readily removable closure for said opening, the other side of the other end portion of said envelope including second means defining a second window opening therein and a second readily removable closure for said second opening, said strap-type body being removably received in said envelope with said first and second fastener means registered with said first and second window openings, the other longitudinal margin of said envelope including an opening formed therein and an integral flexible tube portion having one end portion anchored relative to said other marginal portion about the last mentioned opening and a second end portion extending outward from said other marginal position, said pump and the adjacent end of said tube being loosely removably received in said tube portion.

2. The protective sleeve of claim 1 wherein said second end portion of said tube is closed.

3. The protective sleeve of claim 1 wherein said envelope is constructed of transparent material.

4. The protective sleeve of claim 1 wherein said first and second means include weakened generally rectangular areas of said one and other sides of said envelope and said removble closures comprise the areas of said one and other envelope sides bound by said weakened areas and readily removable from the adjacent portions of said one and other envelope sides.

5. The protective sleeve of claim 1 wherein said envelope and tube portion are of integral one-piece construction.

6. The protective sleeve of claim 1 wherein said open longitudinal margin of said envelope is defined between opposing marginal portions of said one and other sides of said envelope, said opposing margins including co-acting means removably closing said envelope longitudinal margin.

7. The protective sleeve of claim 6 wherein said coacting means removably closing said envelope opposing margins includes interfittingly engageable rib and channel areas extending along said opposing margins.

8. The protective sleeve of claim 7 wherein said envelope and tube portion are of integral one-piece construction.

9. The protective sleeve of claim 8 wherein said first and second means include weakened generally rectangular areas of said one and other sides of said envelope and said removable closures comprise the areas of said one and other envelope sides bound by said weakened areas and readily removable from the adjacent portions of said one and other envelope sides.

10. The protective sleeve of claim 9 wherein said second end portion of said tube is closed.

* * * * *